(12) United States Patent
St. Pierre

(10) Patent No.: US 7,291,180 B2
(45) Date of Patent: *Nov. 6, 2007

(54) MEDICAL STENT AND RELATED METHODS

(75) Inventor: Ernest J. St. Pierre, South Attleboro, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 291 days.

This patent is subject to a terminal disclaimer.

(21) Appl. No.: 10/765,382

(22) Filed: Jan. 27, 2004

(65) Prior Publication Data

US 2004/0186552 A1 Sep. 23, 2004

Related U.S. Application Data

(63) Continuation of application No. 10/032,712, filed on Oct. 24, 2001, now Pat. No. 6,719,804.

(60) Provisional application No. 60/280,809, filed on Apr. 2, 2001.

(51) Int. Cl.
A61F 2/04 (2006.01)

(52) U.S. Cl. .............. 623/23.66; 623/23.65; 623/23.7; 604/8

(58) Field of Classification Search ........ 623/23.7, 623/23.65, 23.66; 604/8
See application file for complete search history.

(56) References Cited

U.S. PATENT DOCUMENTS

| 191,775 | A | 6/1877 | Parsons |
|---|---|---|---|
| 256,590 | A | 4/1882 | Pfarre |
| 386,603 | A | 7/1888 | Parsons |
| 559,620 | A | 5/1896 | Shearer |
| 1,211,928 | A | 1/1917 | Fisher |
| 2,257,369 | A | 9/1941 | Davis |
| 3,087,493 | A | 4/1963 | Schossow |
| 3,314,430 | A | 4/1967 | Alley et al. |
| 3,359,974 | A | 12/1967 | Khalil |
| 3,394,705 | A | 7/1968 | Abramson |
| 3,437,088 | A | 4/1969 | Bielinski |

(Continued)

FOREIGN PATENT DOCUMENTS

CA 1092927 1/1981

(Continued)

OTHER PUBLICATIONS

American Society for Testing and Materials (ASTM) "Designation f 1828-97: Standard Specification for Ureteral Stents[1]", approved Nov. 10, 1997, published May 1998 (pp. 1257-1262).

(Continued)

*Primary Examiner*—Bruce Snow

(57) ABSTRACT

A medical stent is sized for placement in a ureter. The stent includes a first section which includes a first material, defines a lumen, and includes a first coil completing at least one revolution. A second section of the stent includes a second material, defines a lumen, and includes a second coil completing at least one revolution. A third section defines a lumen and is located between the first and second sections. The third section includes a co-extrusion of the first and second materials. One of the first or second sections is harder than the other section.

20 Claims, 8 Drawing Sheets

U.S. PATENT DOCUMENTS

| | | |
|---|---|---|
| 3,485,234 A | 12/1969 | Stevens |
| 3,593,713 A | 7/1971 | Bogoff et al. |
| 3,612,050 A | 10/1971 | Sheridan |
| 3,633,579 A | 1/1972 | Alley et al. |
| 3,726,281 A | 4/1973 | Norton et al. |
| 3,746,003 A | 7/1973 | Blake et al. |
| 3,788,326 A | 1/1974 | Jacobs |
| 3,828,767 A | 8/1974 | Spiroff |
| 3,902,492 A | 9/1975 | Greenhalgh |
| 3,906,954 A | 9/1975 | Baehr et al. |
| 3,920,023 A | 11/1975 | Dye et al. |
| 3,995,623 A | 12/1976 | Blake et al. |
| 4,004,588 A | 1/1977 | Alexander |
| 4,037,599 A | 7/1977 | Raulerson |
| 4,065,264 A | 12/1977 | Lewin |
| 4,069,814 A | 1/1978 | Clemens |
| 4,096,860 A | 6/1978 | McLaughlin |
| 4,099,528 A | 7/1978 | Sorenson et al. |
| 4,100,246 A | 7/1978 | Frisch |
| 4,129,129 A | 12/1978 | Amrine |
| 4,134,402 A | 1/1979 | Marhurkar |
| 4,138,288 A | 2/1979 | Lewin |
| 4,138,457 A | 2/1979 | Rudd et al. |
| 4,144,884 A | 3/1979 | Tersteegen et al. |
| 4,149,535 A | 4/1979 | Volder |
| 4,168,703 A | 9/1979 | Kenigsberg |
| 4,173,981 A | 11/1979 | Mortensen |
| 4,180,068 A | 12/1979 | Jacobsen et al. |
| 4,182,739 A | 1/1980 | Curtis |
| 4,183,961 A | 1/1980 | Curtis |
| 4,202,332 A | 5/1980 | Tersteegen et al. |
| 4,203,436 A | 5/1980 | Grimsrud |
| 4,204,541 A | 5/1980 | Kapitanov |
| 4,212,304 A | 7/1980 | Finney |
| 4,217,895 A | 8/1980 | Sagae et al. |
| 4,223,676 A | 9/1980 | Wuchinich et al. |
| 4,236,520 A | 12/1980 | Anderson |
| 4,239,042 A | 12/1980 | Asai |
| 4,248,234 A | 2/1981 | Assenza et al. |
| 4,257,416 A | 3/1981 | Prager |
| 4,270,535 A | 6/1981 | Bogue et al. |
| 4,307,723 A | 12/1981 | Finney |
| 4,327,722 A | 5/1982 | Groshong et al. |
| 4,334,327 A | 6/1982 | Lyman et al. |
| 4,385,631 A | 5/1983 | Uthmann |
| 4,385,635 A | 5/1983 | Ruiz |
| 4,403,983 A | 9/1983 | Edelman et al. |
| 4,405,313 A | 9/1983 | Sisley et al. |
| 4,405,314 A | 9/1983 | Cope |
| 4,406,656 A | 9/1983 | Hattler et al. |
| 4,413,989 A | 11/1983 | Schjeldahl et al. |
| 4,419,094 A | 12/1983 | Patel |
| D272,651 S | 2/1984 | Marhurkar |
| 4,443,333 A | 4/1984 | Marhurkar |
| 4,451,252 A | 5/1984 | Martin |
| 4,456,000 A | 6/1984 | Schjeldahl et al. |
| 4,484,585 A | 11/1984 | Baier |
| 4,493,696 A | 1/1985 | Uldall |
| 4,504,264 A | 3/1985 | Kelman |
| RE31,873 E | 4/1985 | Howes |
| 4,531,933 A | 7/1985 | Norton et al. |
| 4,540,402 A | 9/1985 | Aigner |
| 4,543,087 A | 9/1985 | Sommercorn et al. |
| 4,553,959 A | 11/1985 | Hickey et al. |
| 4,559,046 A | 12/1985 | Groshong et al. |
| 4,563,170 A | 1/1986 | Aigner |
| 4,563,181 A | 1/1986 | Wijayarathna et al. |
| 4,568,329 A | 2/1986 | Marhurkar |
| 4,568,338 A | 2/1986 | Todd |
| 4,581,012 A | 4/1986 | Brown et al. |
| 4,583,968 A | 4/1986 | Marhurkar |
| 4,596,548 A | 6/1986 | DeVries et al. |
| 4,601,697 A | 7/1986 | Mammolenti et al. |
| 4,601,701 A | 7/1986 | Mueller, Jr. |
| 4,608,993 A | 9/1986 | Albert |
| 4,610,657 A | 9/1986 | Densow |
| 4,619,643 A | 10/1986 | Bai |
| 4,623,327 A | 11/1986 | Marhurkar |
| 4,626,240 A | 12/1986 | Edelman et al. |
| 4,641,652 A | 2/1987 | Hutterer et al. |
| 4,643,711 A | 2/1987 | Bates |
| 4,643,716 A | 2/1987 | Drach |
| 4,648,865 A | 3/1987 | Aigner |
| 4,655,771 A | 4/1987 | Wallstén |
| 4,661,396 A | 4/1987 | Andorf et al. |
| 4,662,404 A | 5/1987 | LeVeen et al. |
| 4,666,426 A | 5/1987 | Aigner |
| 4,671,795 A | 6/1987 | Mulchin |
| 4,675,004 A | 6/1987 | Hadford et al. |
| 4,682,978 A | 7/1987 | Martin |
| 4,687,471 A | 8/1987 | Twardowski et al. |
| 4,692,141 A | 9/1987 | Marhurkar |
| 4,694,838 A | 9/1987 | Wijayarthna et al. |
| 4,713,049 A | 12/1987 | Carter |
| 4,722,725 A | 2/1988 | Sawyer et al. |
| 4,732,152 A | 3/1988 | Wallstén et al. |
| 4,737,146 A | 4/1988 | Amaki et al. |
| 4,738,667 A | 4/1988 | Galloway |
| 4,739,768 A | 4/1988 | Engelson |
| 4,747,840 A | 5/1988 | Ladika et al. |
| 4,753,640 A | 6/1988 | Nichols et al. |
| 4,755,176 A | 7/1988 | Patel |
| 4,769,005 A | 9/1988 | Ginsburg et al. |
| 4,770,652 A | 9/1988 | Marhurkar |
| 4,772,268 A | 9/1988 | Bates |
| 4,773,432 A | 9/1988 | Rydell |
| 4,775,371 A | 10/1988 | Mueller, Jr. |
| 4,776,841 A | 10/1988 | Catalano |
| 4,787,884 A | 11/1988 | Goldberg |
| 4,790,809 A | 12/1988 | Kuntz |
| 4,790,810 A | 12/1988 | Pugh, Jr. et al. |
| 4,795,439 A | 1/1989 | Guest |
| 4,808,155 A | 2/1989 | Marhurkar |
| 4,809,710 A | 3/1989 | Williamson |
| 4,813,429 A | 3/1989 | Eshel et al. |
| 4,813,925 A | 3/1989 | Anderson, Jr. et al. |
| 4,820,262 A | 4/1989 | Finney |
| 4,822,345 A | 4/1989 | Danforth |
| 4,838,881 A | 6/1989 | Bennett |
| 4,842,582 A | 6/1989 | Marhurkar |
| 4,842,590 A | 6/1989 | Tanabe et al. |
| 4,846,791 A | 7/1989 | Hattler et al. |
| 4,846,814 A | 7/1989 | Ruiz |
| 4,863,442 A | 9/1989 | DeMello et al. |
| 4,874,360 A | 10/1989 | Goldberg et al. |
| 4,887,996 A | 12/1989 | Bengmark |
| 4,888,146 A | 12/1989 | Dandeneau |
| 4,894,057 A | 1/1990 | Howes |
| 4,895,561 A | 1/1990 | Marhurkar |
| 4,913,683 A | 4/1990 | Gregory |
| 4,931,037 A | 6/1990 | Wetterman |
| 4,950,228 A | 8/1990 | Knapp, Jr. et al. |
| 4,954,126 A | 9/1990 | Wallsten |
| 4,960,409 A | 10/1990 | Catalano |
| 4,960,411 A | 10/1990 | Buchbinder |
| 4,961,809 A | 10/1990 | Martin |
| 4,963,129 A | 10/1990 | Rusch |
| 4,973,301 A | 11/1990 | Nissenkorn |
| 4,976,690 A | 12/1990 | Solar et al. |
| 4,978,341 A | 12/1990 | Niederhauser |
| 4,981,482 A | 1/1991 | Ichikawa |
| 4,985,022 A | 1/1991 | Fearnot et al. |
| 4,986,814 A | 1/1991 | Burney et al. |
| 4,990,133 A | 2/1991 | Solazzo |

| Patent No. | Date | Inventor(s) |
|---|---|---|
| 4,994,071 A | 2/1991 | MacGregor |
| 4,995,863 A | 2/1991 | Nichols et al. |
| 4,995,865 A | 2/1991 | Gahara et al. |
| 4,995,868 A | 2/1991 | Brazier |
| 4,998,919 A | 3/1991 | Schnepp-Pesch et al. |
| 5,004,456 A | 4/1991 | Botterbusch et al. |
| 5,009,636 A | 4/1991 | Wortley et al. |
| 5,013,296 A | 5/1991 | Buckberg et al. |
| 5,019,102 A | 5/1991 | Hoene |
| 5,026,377 A | 6/1991 | Burton et al. |
| 5,029,580 A | 7/1991 | Radford et al. |
| 5,041,083 A | 8/1991 | Tsuchida et al. |
| 5,053,004 A | 10/1991 | Markel et al. |
| 5,053,023 A | 10/1991 | Martin |
| 5,057,073 A | 10/1991 | Martin |
| 5,061,275 A | 10/1991 | Wallstén et al. |
| 5,078,720 A | 1/1992 | Burton et al. |
| 5,085,629 A | 2/1992 | Goldberg et al. |
| 5,116,309 A | 5/1992 | Coll |
| 5,124,127 A | 6/1992 | Jones et al. |
| 5,129,910 A | 7/1992 | Phan et al. |
| 5,135,487 A | 8/1992 | Morrill et al. |
| 5,135,599 A | 8/1992 | Martin et al. |
| 5,141,502 A | 8/1992 | Macaluso, Jr. |
| 5,147,370 A | 9/1992 | McNamara et al. |
| 5,149,330 A | 9/1992 | Brightbill |
| 5,156,592 A | 10/1992 | Martin et al. |
| 5,156,596 A | 10/1992 | Balbierz et al. |
| 5,156,857 A | 10/1992 | Wang et al. |
| 5,160,325 A | 11/1992 | Nichols et al. |
| 5,167,623 A | 12/1992 | Cianci et al. |
| 5,171,216 A | 12/1992 | Dasse et al. |
| 5,176,625 A | 1/1993 | Brisson |
| 5,176,626 A | 1/1993 | Soehendra |
| 5,178,803 A | 1/1993 | Tsuchida et al. |
| 5,188,593 A | 2/1993 | Martin |
| 5,190,520 A | 3/1993 | Fenton, Jr. et al. |
| 5,195,962 A | 3/1993 | Martin et al. |
| 5,197,951 A | 3/1993 | Marhurkar |
| 5,207,648 A | 5/1993 | Gross |
| 5,209,723 A | 5/1993 | Twardowski et al. |
| 5,211,627 A | 5/1993 | William |
| 5,221,253 A | 6/1993 | Coll |
| 5,221,255 A | 6/1993 | Marhurkar et al. |
| 5,221,256 A | 6/1993 | Marhurkar |
| 5,222,949 A | 6/1993 | Kaldany |
| 5,224,953 A | 7/1993 | Morgentalker |
| 5,234,663 A | 8/1993 | Jones et al. |
| 5,240,677 A | 8/1993 | Jones et al. |
| 5,242,395 A | 9/1993 | Maglinte |
| 5,246,445 A | 9/1993 | Yachia et al. |
| 5,250,038 A | 10/1993 | Melker et al. |
| 5,261,879 A | 11/1993 | Brill |
| 5,269,802 A | 12/1993 | Garber |
| 5,275,597 A | 1/1994 | Higgins et al. |
| 5,279,560 A | 1/1994 | Morrill et al. |
| 5,282,784 A | 2/1994 | Willard |
| 5,292,305 A | 3/1994 | Boudewijn et al. |
| 5,292,321 A | 3/1994 | Lee |
| 5,295,954 A | 3/1994 | Sachse |
| 5,308,322 A | 5/1994 | Tennican et al. |
| 5,308,342 A | 5/1994 | Sepetka et al. |
| 5,318,532 A | 6/1994 | Frassica |
| 5,324,274 A | 6/1994 | Martin |
| 5,330,449 A | 7/1994 | Prichard et al. |
| 5,338,311 A | 8/1994 | Marhurkar |
| 5,342,301 A | 8/1994 | Saab |
| 5,342,386 A | 8/1994 | Trotta |
| 5,342,387 A | 8/1994 | Summers |
| 5,346,467 A | 9/1994 | Coll |
| 5,346,471 A | 9/1994 | Raulerson |
| 5,348,536 A | 9/1994 | Young et al. |
| 5,354,263 A | 10/1994 | Coll |
| 5,354,309 A | 10/1994 | Schnepp-Pesch et al. |
| 5,356,423 A | 10/1994 | Tihon et al. |
| 5,356,424 A | 10/1994 | Buzerak et al. |
| 5,358,689 A | 10/1994 | Jones et al. |
| 5,360,397 A | 11/1994 | Pinchuk |
| 5,364,340 A | 11/1994 | Coll |
| 5,364,344 A | 11/1994 | Beattie et al. |
| 5,366,464 A | 11/1994 | Belknap |
| 5,372,600 A | 12/1994 | Beyar et al. |
| 5,374,245 A | 12/1994 | Marhurkar |
| 5,378,230 A | 1/1995 | Marhurkar |
| 5,380,270 A | 1/1995 | Ahmadzadeh |
| 5,380,276 A | 1/1995 | Miller et al. |
| 5,383,928 A | 1/1995 | Scott et al. |
| 5,391,196 A | 2/1995 | Devonec |
| 5,395,316 A | 3/1995 | Martin |
| 5,399,172 A | 3/1995 | Martin et al. |
| 5,401,257 A | 3/1995 | Chevalier, Jr. et al. |
| 5,403,291 A | 4/1995 | Abrahamson |
| 5,405,320 A | 4/1995 | Twardowski et al. |
| 5,405,329 A | 4/1995 | Durand |
| 5,405,341 A | 4/1995 | Martin |
| 5,405,380 A | 4/1995 | Gianotti et al. |
| 5,411,490 A | 5/1995 | Tennican et al. |
| 5,440,327 A | 8/1995 | Stevens |
| 5,445,624 A | 8/1995 | Jimenez |
| 5,449,372 A | 9/1995 | Schmaltz et al. |
| 5,451,206 A | 9/1995 | Young |
| 5,464,398 A | 11/1995 | Haindl |
| 5,470,322 A | 11/1995 | Horzewski et al. |
| 5,472,417 A | 12/1995 | Martin et al. |
| 5,472,432 A | 12/1995 | Martin |
| 5,472,435 A | 12/1995 | Sutton |
| 5,480,380 A | 1/1996 | Martin |
| 5,484,424 A | 1/1996 | Cottenceau et al. |
| 5,486,159 A | 1/1996 | Mahurkar |
| 5,489,278 A | 2/1996 | Abrahamson |
| 5,509,897 A | 4/1996 | Twardowski et al. |
| 5,514,100 A | 5/1996 | Marhurkar |
| 5,514,176 A | 5/1996 | Bosley, Jr. |
| 5,514,178 A | 5/1996 | Torchio |
| 5,520,697 A | 5/1996 | Lindenberg et al. |
| 5,522,807 A | 6/1996 | Luther |
| 5,527,337 A | 6/1996 | Stack et al. |
| 5,531,741 A | 7/1996 | Barbacci |
| 5,533,985 A | 7/1996 | Wang |
| 5,540,713 A | 7/1996 | Schnepp-Pesch et al. |
| 5,542,937 A | 8/1996 | Chee et al. |
| 5,553,665 A | 9/1996 | Gentry |
| 5,554,136 A | 9/1996 | Luther |
| 5,556,390 A | 9/1996 | Hicks |
| 5,562,641 A | 10/1996 | Flomenblit et al. |
| 5,569,182 A | 10/1996 | Twardowski et al. |
| 5,569,184 A | 10/1996 | Crocker et al. |
| 5,569,195 A | 10/1996 | Saab |
| 5,569,215 A | 10/1996 | Crocker |
| 5,569,218 A | 10/1996 | Berg |
| 5,571,093 A | 11/1996 | Cruz et al. |
| 5,573,508 A | 11/1996 | Thornton |
| 5,599,291 A | 2/1997 | Balbierz et al. |
| 5,601,538 A | 2/1997 | Deem |
| 5,613,980 A | 3/1997 | Chauhan |
| 5,622,665 A | 4/1997 | Wang |
| 5,624,413 A | 4/1997 | Markel et al. |
| 5,630,794 A | 5/1997 | Lax et al. |
| 5,632,734 A | 5/1997 | Galel et al. |
| 5,639,278 A | 6/1997 | Dereume et al. |
| 5,643,222 A | 7/1997 | Marhurkar |
| 5,647,843 A | 7/1997 | Mesrobian et al. |
| 5,649,909 A | 7/1997 | Cornelius |
| 5,653,689 A | 8/1997 | Buelna et al. |
| 5,658,263 A | 8/1997 | Dang et al. |
| 5,667,486 A | 9/1997 | Mikulich et al. |

| | | |
|---|---|---|
| 5,674,277 A | 10/1997 | Freitag |
| 5,676,697 A | 10/1997 | McDonald |
| 5,681,274 A | 10/1997 | Perkins et al. |
| 5,683,640 A | 11/1997 | Miller et al. |
| 5,685,862 A | 11/1997 | Marhurkar |
| 5,685,867 A | 11/1997 | Twardowski et al. |
| 5,695,479 A | 12/1997 | Jagpal |
| 5,695,482 A | 12/1997 | Kaldany |
| 5,695,789 A | 12/1997 | Harris |
| 5,707,386 A | 1/1998 | Schnepp-Pesch et al. |
| 5,709,874 A | 1/1998 | Hanson et al. |
| 5,718,862 A | 2/1998 | Thompson |
| 5,725,814 A | 3/1998 | Harris |
| 5,730,733 A | 3/1998 | Mortier et al. |
| 5,755,774 A | 5/1998 | Pinchuk |
| 5,762,630 A | 6/1998 | Bley et al. |
| 5,766,209 A | 6/1998 | Devonec |
| 5,769,868 A | 6/1998 | Yock |
| 5,772,641 A | 6/1998 | Wilson |
| 5,776,161 A | 7/1998 | Globerman |
| 5,791,036 A | 8/1998 | Goodin et al. |
| 5,792,105 A | 8/1998 | Lin et al. |
| 5,792,124 A | 8/1998 | Horrigan et al. |
| 5,792,400 A | 8/1998 | Talja et al. |
| 5,795,319 A | 8/1998 | Ali |
| 5,795,326 A | 8/1998 | Simán |
| 5,830,179 A | 11/1998 | Mikus et al. |
| 5,830,184 A | 11/1998 | Basta |
| 5,830,196 A | 11/1998 | Hicks |
| 5,836,925 A | 11/1998 | Soltesz |
| 5,843,028 A | 12/1998 | Weaver et al. |
| 5,843,175 A | 12/1998 | Frantzen |
| 5,851,203 A | 12/1998 | van Muiden |
| 5,860,999 A | 1/1999 | Schnepp-Pesch et al. |
| 5,865,815 A | 2/1999 | Tihon |
| 5,876,417 A | 3/1999 | Devonec et al. |
| 5,895,378 A | 4/1999 | Nita |
| 5,897,537 A | 4/1999 | Berg et al. |
| 5,899,891 A | 5/1999 | Racz |
| 5,899,892 A | 5/1999 | Mortier et al. |
| 5,906,640 A | 5/1999 | Penn et al. |
| 5,911,715 A | 6/1999 | Berg et al. |
| 5,928,217 A | 7/1999 | Mikus et al. |
| 5,947,939 A | 9/1999 | Mortier et al. |
| 5,961,511 A | 10/1999 | Mortier et al. |
| 5,964,744 A | 10/1999 | Balbierz et al. |
| 5,964,771 A | 10/1999 | Beyar et al. |
| 5,976,120 A | 11/1999 | Chow et al. |
| 5,980,505 A | 11/1999 | Wilson |
| 5,984,907 A | 11/1999 | McGee et al. |
| 6,007,478 A | 12/1999 | Siess et al. |
| 6,019,789 A | 2/2000 | Dinh et al. |
| 6,033,413 A | 3/2000 | Mikus et al. |
| 6,135,992 A | 10/2000 | Wang |
| 6,139,536 A | 10/2000 | Mikus et al. |
| 6,620,202 B2 | 9/2003 | Bottcher et al. |
| 2002/0143389 A1 | 10/2002 | St. Pierre |

FOREIGN PATENT DOCUMENTS

| | | |
|---|---|---|
| CA | 1150122 | 7/1983 |
| CA | 1167727 | 5/1984 |
| CA | 1193508 | 9/1985 |
| CA | 1219785 | 3/1987 |
| CA | 1225299 | 11/1987 |
| DE | 2259865 | 6/1974 |
| DE | 3112762 C2 | 1/1983 |
| DE | 35 17 813 A1 | 11/1986 |
| DE | 37 40 288 C1 | 4/1989 |
| DE | 41 03 573 A1 | 8/1992 |
| DE | 41 34 030 C2 | 4/1993 |
| DE | 93 14 585.3 | 1/1994 |
| EP | 0036642 A2 | 9/1981 |
| EP | 0079719 A1 | 5/1983 |
| EP | 0101890 A1 | 3/1984 |
| EP | 0101890 B1 | 3/1984 |
| EP | 0144525 A2 | 6/1985 |
| EP | 0168136 A1 | 1/1986 |
| EP | 0183421 A2 | 6/1986 |
| EP | 0 326 908 A2 | 8/1989 |
| EP | 0333308 A2 | 9/1989 |
| EP | 0183421 B1 | 4/1990 |
| EP | 0386408 A1 | 9/1990 |
| EP | 0490459 A1 | 6/1992 |
| EP | 0490459 B1 | 6/1992 |
| EP | 0554722 A1 | 8/1993 |
| EP | 0 876 803 A2 | 11/1998 |
| EP | 0 916 362 A1 | 5/1999 |
| FR | 1285953 | 1/1962 |
| FR | 1508959 | 12/1967 |
| FR | 2297640 | 8/1976 |
| FR | 2530958 A1 | 2/1984 |
| FR | 2 611 486 | 9/1988 |
| GB | 2017499 A | 10/1979 |
| GB | 2156220 A | 10/1985 |
| GB | 2235384 A | 3/1991 |
| JP | 57-90150 | 6/1982 |
| JP | 62-20830 | 8/1994 |
| WO | WO 84/04043 | 10/1984 |
| WO | WO 95/26763 | 10/1995 |
| WO | WO 95/28982 | 11/1995 |
| WO | WO 95/29051 | 11/1995 |
| WO | WO 95/35130 | 12/1995 |
| WO | WO 97/10858 | 3/1997 |
| WO | WO 97/17094 | 5/1997 |
| WO | WO 97/37699 | 10/1997 |
| WO | WO 97/37718 | 10/1997 |
| WO | WO 97/39788 | 10/1997 |
| WO | WO 98/22159 | 5/1998 |
| WO | WO 98/43695 | 10/1998 |
| WO | WO 98/56313 | 12/1998 |
| WO | WO 99/39661 | 8/1999 |
| WO | WO 99/49811 | 10/1999 |
| WO | WO 02/078778 | 10/2002 |

OTHER PUBLICATIONS

Bard Access Systems Vas-Cath Incorporated Catalog date unknown.
Bard/angiomed product brochure, 1988.
Bard brochure, "Introducing The Bard Urinary Diversion Stent," 1984.
Bard product brochure, "Introducing The Bard Pediatric Urethral Stent," 1983.
Bard product brochure, "Stents To Satisfy The Urologist: . . . ", 1988.
Bard Urological Division product catalog, 1990, (pp. 1-3, A1-A30, D7-D26; last page).
Bigongiari et al., "Conversion of Percutaneous Ureteral Stent To Indwelling Pigtail Stent Over Guidewire," Urology, May 1980, vol. XV, No. 5, (pp. 461-465).
Birch et al., "Tethered Ureteric Stents—a Clinical Assessment," British Journal of Urology, 1988, vol. 62, (pp. 409-411).
Camacho et al. "Double-Ended Pigtail Ureteral Stent: Useful Modifcation to Single End Ureteral Stent," Urology, May 1979, vol. XIII, No. 5, (pp. 516-520).
Circon Surgitek package insert for Tecoflex® Quadra-Coil® Multi-Length Ureteral Stents, two pages (1998) and 2 photographs of Quadra-Coil™ Ureteral Stent.
Collier et al., "Proximal Stent Displacement As Complication of Pigtail Ureteral Stent," Urology, Apr. 1979, vol. XIII, No. 4, (pp. 372-375).
Cook Critcal Care Catalog, "Products for Dialysis" pp. 3-15 (1989).
Cook Critical Care Catalog, "Uldall Double Lumen Hemodialysis Catheter Trays" date unknown.
Cook Urological catalog, "Urological Surgical Products," 1990-1991, (pp. 1-3, 7-29, 48-148; last page).

Cook Urological product brochure,"Ureteral Stents," 1987, (pp. 1-23; last page).
Cook Urological Catalog, 1995, (pp. 1-2, 9-41, 63-173; last page).
Cook Urological product brochure, "Filiform Ureteral Multi-Length Silicone Stent Sets," 1989.
Culkin, "Complications of Ureteral Stents," *Infections in Urology*, Sep./Oct. 1996, (pp. 139, 142-143).
Hackethorn et al., "Antegrade Internal Ureteral Stenting: A Technical Refinement," *Radiology*, Jul. 1985, vol. 156, No. 3, (pp. 827-828).
Hepperlen et al., "Self-Retained Internal Ureteral Stents: A New Approach," *The Journal of Urology*, Jun. 1978, vol. 119, (pp. 731-734).
Horizon Medical Products Catalog date unknown.
Mardis, "Evaluation of Polymeric Materials for Endourologic Devices," *Seminars in Interventional Radiology*, Mar. 1987, vol. 4, No. 1, (pp. 36-45).
Mardis et al., "Double Pigtail Ureteral Stent," *Urology*, Jul. 1979, vol. XIV, No. 1, (pp. 23-26).
Mardis et al., "Comparative Evaluation of Materials Used for Internal Ureteral Stents," *Journal of Endourology*, 1993, vol. 7, No. 2, (pp. 105-115).
Mardis et al., "Guidewires, Ureteral Catheters, and Stents," *Color Atlas/Text of Ureteroscopy*, 1993 New York, Igaku-Shoin, Ch. 5, (pp. 65-84).
Mardis et al., "Polyethylene Double-Pigtail Ureteral Stents," *Urologic Clinics of North America*, Feb. 1982, vol. 9, No. 1, (pp. 95-101).
Mardis et al., "Ureteral Stents Use and Complications," *Problems in Urology*, Jun. 1992 vol. 6, No. 2, (pp. 296-306).
Mardis et al., "Ureteral Stents-Materials," *Urologic Clinics of North America*, Aug. 1988, vol. 15, No. 3, (pp. 471-479).
McIntosh, et al. J.A.M.A. 169(8): 137-8 (1959).
MEDCOMP Catalog, "Hemodialysis Products" pp. 1-11, 14-16, 19-27, 30-36 date unknown.
MEDCOMP Catalog "Schon Twin-Cath" date unknown.
Microvasive Catalog, "J-Maxx™ Ureteral Stents with Hydro Plus™," date unknown, (2 pages).
Microvasive Catalog, "Mardis Soft Variable Length Ureteral Stents," date unknown, (pp. 6-39-6-40).
Microvasive Catalog, "Mardis Soft Variable Length Ureteral Stents with Hydro Plus™ Coating," date unknown, (p. 6-37).
Microvasive Catalog,"Percutaneous Nephrostomy Catheters with Locking Loop," date unknown, (p. 4-49).
Microvasive Catalog,"Ureteral Stents and Ureteral Catheters," date unknown, pp. 6-1-6-10.
Microvasive Products for Urology, 1992, (pp. 6-1-6-7; 6-9-6-11; 6-13-6-23; 6-25-6-27; 6-29-6-37; 6-39-6-43; 6-456-49; 6-51; 6-53).
Microvasive Products for Urology, 1994, (pp. 6-1-6-7; 6-9-6-11; 6-13-6-23, 6-25-6-27; 6-29-6-37; 6-39-6-43; 6-456-49; 6-51; 6-53).
Microvasive Products for Endourology, 1996, (pp. 6-1-6-8; 6-13-6-15; 6-17-6-19; 6-21-6-23; 6-25-6-29; 6-31-6-46; 6-51-6-55; 6-61-6-64).
Microvasive Products for Endourology, 1997, (pp. 6-1-6-8; 6-13-6-15; 6-17-6-19; 6-21-6-23; 6-25-6-29; 6-31-6-40; 6-43-6-46; 6-51-6-55).
Minkov et al., "Our Experience in the Application of the Biocompatible Indwelling Ureteral Stents," *International Urology and Nephrology*, 1986, 18 (4), (pp. 403-409).
Quinton Instrument Co. Catalog, "Hemodialysis and Apheresis" (1994).
Quinton Instrument Co. Catalog, "Hemodialysis and Apheresis" (1995).
Quinton Instrument Co. Catalog, "Oncology/Critical Care" (1993).
Riesenfeld, et al. "Surface Modification of Functionally Active Heparin," Medical Device Technology (Mar. 1995).
Rutner et al., "Percutaneous Pigtail Nephrostomy," *Urology*, Oct. 1979, vol. XIV, No. 4, (pp. 337-340).
Sadlowski et al., "New Technique For Percutaneous Nephrostomy Under Ultrasound Guidance," *Journal of Urology*, May 1979, vol. 121, (pp. 559-561).
Stables, "Percutaneous Nephrostomy: Techniques, Indications, and Results," *Urologic Clinics of North America*, Feb. 1982, vol. 9, No. 1, (pp. 15-29).
Surgitek brochure, "The Solution Is Perfectly Clear," 1990.
Surgitek Catalog, "The Multi-Flex Hydrophilic Coated Ureteral Stent," 1993, (4 pages).
"Triple Lumen Catheter" p. 3 (First! An Information Service of Individual, Inc., Sep. 25, 1995).
"Ureteroscopic Procedures—Technical Advances," *Color Atlas/Text of Ureteroscopy*, 1993 New York, Igaku-Shoin, p. 281.
International Search Report for International Patent Application No. PCT/US02/09357, dated Aug. 8, 2002, 3 pages.

| Stent Description | French Size | Renal Coil Strength (gram-force) |
|---|---|---|
| One Embodiment of Stent According to Invention | 5 | 26.3 |
| Percuflex® Plus Stent (Boston Scientific Corporation, Natick, MA) | 4.8 | 17.3 |
| Contour™ Stent (Boston Scientific Corporation, Natick, MA) | NA | NA |
| In-Lay™ Stent (C.R. Bard, Inc., Murray Hill, New Jersey) | 4.7 | 19.7 |
| Surgitek H2O™ Stent (Circon Corporation, Santa Barbara, CA) | 4.5 | 18.5 |
| Cook Sof-Flex™ AQ Stent (Cook Urological Inc., Spencer, IN) | 4.7 | 14.3 |
| Cook Endo-Sof™ AQ Stent (Cook Urological Inc., Spencer, IN) | 5 | 21.9 |
| One Embodiment of Stent According to Invention | 6 | 55.4 |
| Percuflex® Plus Stent (Boston Scientific Corporation, Natick, MA) | 6 | 32.56 |
| Contour™ Stent (Boston Scientific Corporation, Natick, MA) | 6 | 18.43 |
| In-Lay™ Stent (C.R. Bard, Inc., Murray Hill, New Jersey) | 6 | 37.69 |
| Surgitek H2O™ Stent (Circon Corporation, Santa Barbara, CA) | 6 | 26.59 |
| Cook Sof-Flex™ AQ Stent (Cook Urological Inc., Spencer, IN) | 6 | 25.19 |
| Cook Endo-Sof™ AQ Stent (Cook Urological Inc., Spencer, IN) | 6 | 40.23 |
| One Embodiment of Stent According to Invention | 7 | 83.3 |
| Percuflex® Plus Stent (Boston Scientific Corporation, Natick, MA) | 7 | 52.07 |
| Contour™ Stent (Boston Scientific Corporation, Natick, MA) | 7 | 29.61 |
| In-Lay™ Stent (C.R. Bard, Inc., Murray Hill, New Jersey) | 7 | 58.08 |
| Surgitek H2O™ Stent (Circon Corporation, Santa Barbara, CA) | 7 | 46.15 |
| Cook Sof-Flex™ AQ Stent (Cook Urological Inc., Spencer, IN) | 7 | 32.6 |
| Cook Endo-Sof™ AQ Stent (Cook Urological Inc., Spencer, IN) | 7 | 51.48 |
| One Embodiment of Stent According to Invention | 8 | 90.6 |
| Percuflex® Plus Stent (Boston Scientific Corporation, Natick, MA) | 8 | 77.7 |
| Contour™ Stent (Boston Scientific Corporation, Natick, MA) | 8 | 39.56 |
| In-Lay™ Stent (C.R. Bard, Inc., Murray Hill, New Jersey) | 8 | 58.39 |
| Surgitek H2O™ Stent (Circon Corporation, Santa Barbara, CA) | 8 | 76.95 |
| Cook Sof-Flex™ AQ Stent (Cook Urological Inc., Spencer, IN) | 8 | 74.7 |
| Cook Endo-Sof™ AQ Stent (Cook Urological Inc., Spencer, IN) | 8 | No Data |

FIG. 10

| FRENCH SIZE | AVERAGE O.D. | I.D. |
|---|---|---|
| 4.3 | .057±.001 | .039±.001 |
| 5.3 | .070±.002 | .046±.002 |
| 6.3 | .083±.002 | .051±.002 |
| 7.3 | .095±.002 | .059±.002 |
| 8.3 | .107±.002 | .066±.002 |

FIG. 11

MEDICAL STENT AND RELATED METHODS

CROSS-REFERENCE TO RELATED APPLICATION

This application is a continuation of Ser. No. 10/032,712, filed Oct. 24, 2001, now U.S. Pat. No. 6,719,804, which claims priority to and the benefit of Ser. No. 60/280,809, filed on Apr. 2, 2001, the entire disclosure of each application being incorporated herein by reference.

TECHNICAL FIELD

The present invention relates to medical stents and related methods. More specifically, the invention relates to medical stents having one end section which is softer than a section at the other end of the stent.

BACKGROUND INFORMATION

Fluid sometimes needs to be drained from a body. For example, urine formed in one or both kidneys might need to be drained into the bladder. One way to accomplish such drainage is to use a medical device that conveys the fluid (e.g., urine) through a lumen. Such devices include stents and catheters. Existing stents can be uncomfortable for the patient, especially when they reside in the ureter between the kidney and the bladder, or can be difficult for a medical professional to place in a patient.

SUMMARY OF THE INVENTION

The present invention provides medical stents for facilitating drainage of fluid and methods for placing such stents. For example, such stents can be placed in a ureter to facilitate drainage of fluid from a patient's kidney to a patient's bladder. Generally, stents according to the invention have a "softer" end and a "harder" end. The harder end generally resides in the patient's kidney while the softer end generally resides in the patient's bladder. The harder end transitions to the softer end in a transition section produced by a co-extrusion process where deposition of a first material is gradually ceased and deposition of a second is gradually increased. The harder end is suited to retain the stent in the patient's kidney and/or facilitate placement in a patient while the softer end is suited to increase patient comfort and/or, to a degree, retain the stent in the patient's bladder. Such stents also are useful in other situations such as biliary drainage or, generally, where one body structure is drained to another body structure.

In one embodiment, a medical stent includes a single-piece, extruded stent body which does not substantially soften when exposed to a temperature of a human body. At least a portion of the stent body can be sized for placement in a ureter, and at least a section of the stent body can define holes therethrough. The stent body itself includes a first section, a second section, and a third section defining a lumen and located between the first and second sections. The first section includes a first material having a first durometer value while the second section includes a second material having a second durometer value. The second durometer value is greater than the first durometer value. The third section includes a co-extrusion of the first and second materials that is disposed between the first coil and the second coil. The first section defines a lumen and includes a first coil completing at least one revolution, and the second section defines a lumen and includes a second coil completing at least one revolution. An outer surface of the third section smoothly transitions to outer surfaces of the first and second sections immediately proximate the third section, and an inner diameter of the third section is substantially constant through the third section and on either side of the third section immediately proximate to the third section in the first and second sections.

The embodiment described above, or those described below, can have any of the following features. The first material can include ethylene vinyl acetate. The stent body can include a mark on an outer surface of the stent body. The stent body can include a radiopaque marking. The stent can have an outer diameter of about 4 French to about 9 French. The stent can have an inner diameter of about 0.38 inches. The stent can have a length of about 10 cm to about 30 cm as measured between the coils. The stent can include a hydrophilic coating. The first material can have a durometer value of about 70 to about 90 on a Shore A scale. The second material can have a durometer value of about 80 to about 95 on a Shore A scale. At least one of the coils can be asymmetric. An end of at least one of the first section and the second section can be tapered. A cross-section of the lumen in at least one of the first, second, and third sections can be circular. A cross-section of at least one of the first, second, and third sections can be circular. At least one of the first, second, and third section can include a radiopaque material.

In another embodiment, a medical stent includes a single-piece, extruded stent body which does not substantially soften when exposed to a temperature of a human body. At least a portion of the stent body can be sized for placement in a ureter, and at least a section of the stent body can define holes therethrough. The stent body itself includes a first section, a second section, and a third section defining a lumen and located between the first and second sections. The first section defines a lumen and includes a first coil completing at least one revolution, and the second section defines a lumen and includes a second coil completing at least one revolution. The first section includes a first material, and the second section includes a second material. The first coil has a first retention strength, and the second coil has a second retention strength. The second retention strength is greater than the first retention strength. The third section includes a co-extrusion of the first and second materials that is disposed between the first coil and the second coil. An outer surface of the third section smoothly transitions to outer surfaces of the first and second sections immediately proximate the third section. An inner diameter of the third section is substantially constant through the third section and on either side of the third section immediately proximate to the third section in the first and second sections.

In another aspect of the invention, a method for placing a medical stent includes inserting a medial stent, including any of the stents described above or below with any of the features described above or below, into a ureter.

BRIEF DESCRIPTION OF THE DRAWINGS

In the drawings, like reference characters generally refer to the same parts throughout the different views. Also, the drawings are not necessarily to scale, emphasis instead generally being placed upon illustrating principles of the invention.

FIG. 10 is a table containing renal coil retention strength values.

FIG. 11 is a table containing inner and outer diameter sizes for certain embodiments of the invention.

DESCRIPTION

The present invention provides medical stents for facilitating drainage of fluid and methods for placing such stents. For example, such stents are placed in a ureter to facilitate drainage of fluid from a patient's kidney to a patient's bladder. Generally, stents according to the invention have a "softer" end and a "harder" end. The harder end generally resides in the patient's kidney while the softer end generally resides in the patient's bladder. The harder end transitions to the softer end in a transition section produced by a co-extrusion process where deposition of a first material is gradually ceased and deposition of a second is gradually increased. As used herein, the terms "hard" and "soft," and various grammatical forms thereof, are general terms meant to generally refer to a difference in properties, including, but not limited to, a difference in the durometer value of all or some of the material(s) used to construct a stent (for example, a higher durometer value of one material used in constructing a section of a stent (even if other materials are also used to construct that same section of stent) can mean "hard" and a lower durometer value of one material used in constructing another section of a stent (even if other materials are also used to construct that same section of stent) can mean "soft"), a difference in the retention strengths of the coils on either end of a stent (for example, a higher retention strength can mean "hard" and a lower retention strength can mean "soft"), a difference in stiffness (for example, a more stiff material/section of stent can be "hard" and a less stiff material/section of stent can be "soft"), or other differences between material(s) used to construct a stent or between sections of a stent that those skilled in the art would consider "hard" and/or "soft."

On the one hand, some ureteral stents that are in use are made from a higher durometer material to facilitate placement and retention in the body. However, these firmer stents may contribute to some patient discomfort issues. On the other hand, some ureteral stents that are in use are made from a lower durometer material in an effort to enhance patient comfort. However, these softer stents may be difficult to place and may migrate once placed in the patient's body.

In contrast, stents according to the invention have a harder end at one end and a softer end at the other end. This construction is desirable because the harder end is suited for placing the stent in the patient's kidney and/or to retain the stent in the patient's kidney while the softer end is suited to increase patient comfort and/or, to a degree, retain the stent in the patient's bladder. Accordingly, stents according to the invention are designed to incorporate multiple desirable features into a single stent.

Figure 1:
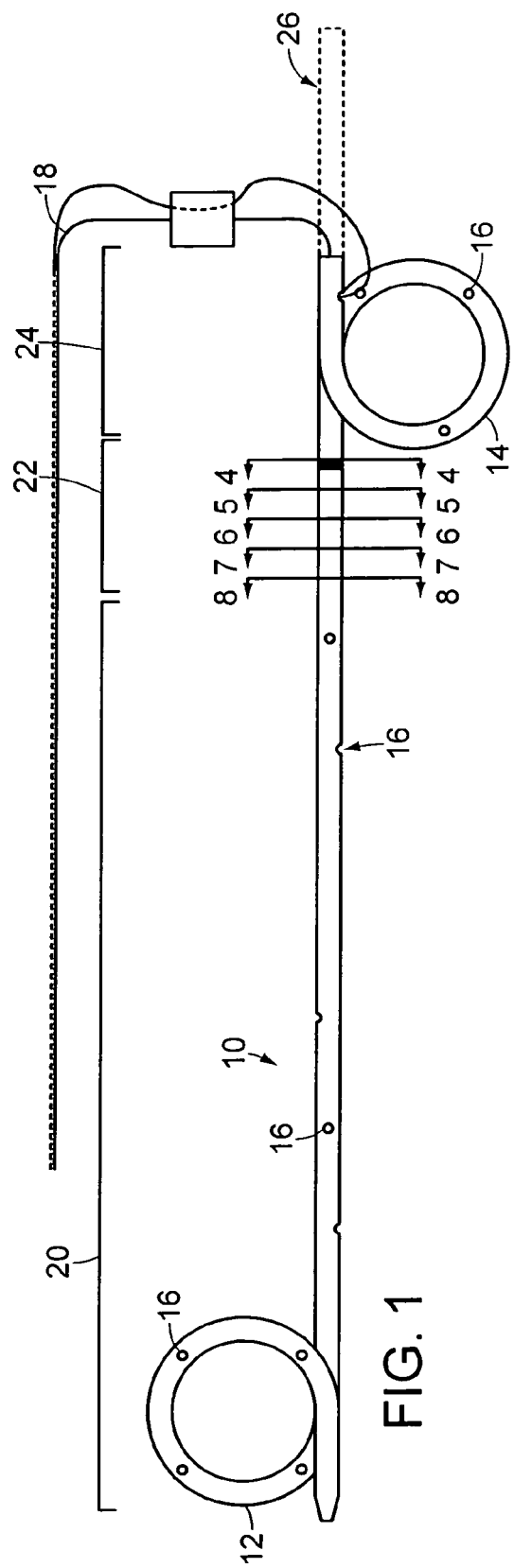
FIG. 1 is a schematic rendering of a stent according to the invention.
Figure 2:
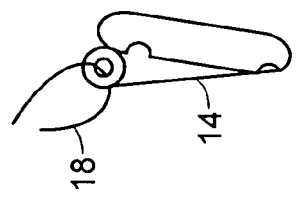
FIG. 2 is a schematic end-on view of the stent of FIG. 1.

Referring to FIGS. 1 and 2, a schematic representation of one embodiment of a stent 10 according to the invention is shown. Generally, the stent 10 has three sections 20, 22, 24. A first section 24 is located at the proximal end (as used herein, proximal refers to the end of a stent closest a medical professional when placing a stent in a patient) of the stent 10. A second section 20 is located at the distal end (as used herein, distal refers to the end of a stent furthest from a medical professional when placing a stent in a patient) of the stent 10. A third section 22 is located between the first 24 and second sections 20. The location of the sections 20, 22, 24 as shown in FIG. 1 is approximate, emphasis instead being placed on illustrating the principles of the invention. The first section 24 has a first coil 14 that makes more than one revolution. The first coil 14 is offset from the general axis of the stent 10 (best seen in FIG. 2). The second section 20 has a second coil 12 which also makes more than one revolution and also is offset from the general axis of the stent 10. The second coil 12 has a tapered tip (which, in certain embodiments, can be relatively long). Additionally, or in the alternative, the tip can be beveled. Holes 16 (only some of the holes are labeled) in the outer surface of the stent 10 are located along the length of stent 10. These holes 16 allow the outside environment to communicate with a lumen inside the stent 10. The holes 16 can be placed in many configurations, one of which is shown in FIG. 1. In alternate embodiments, holes can be placed along a section or sections of a stent. Additionally, a suture 18 is attached to the first section 24 and is used for placing the stent 10 in a desired position as well as removing the stent 10.

Figure 3:
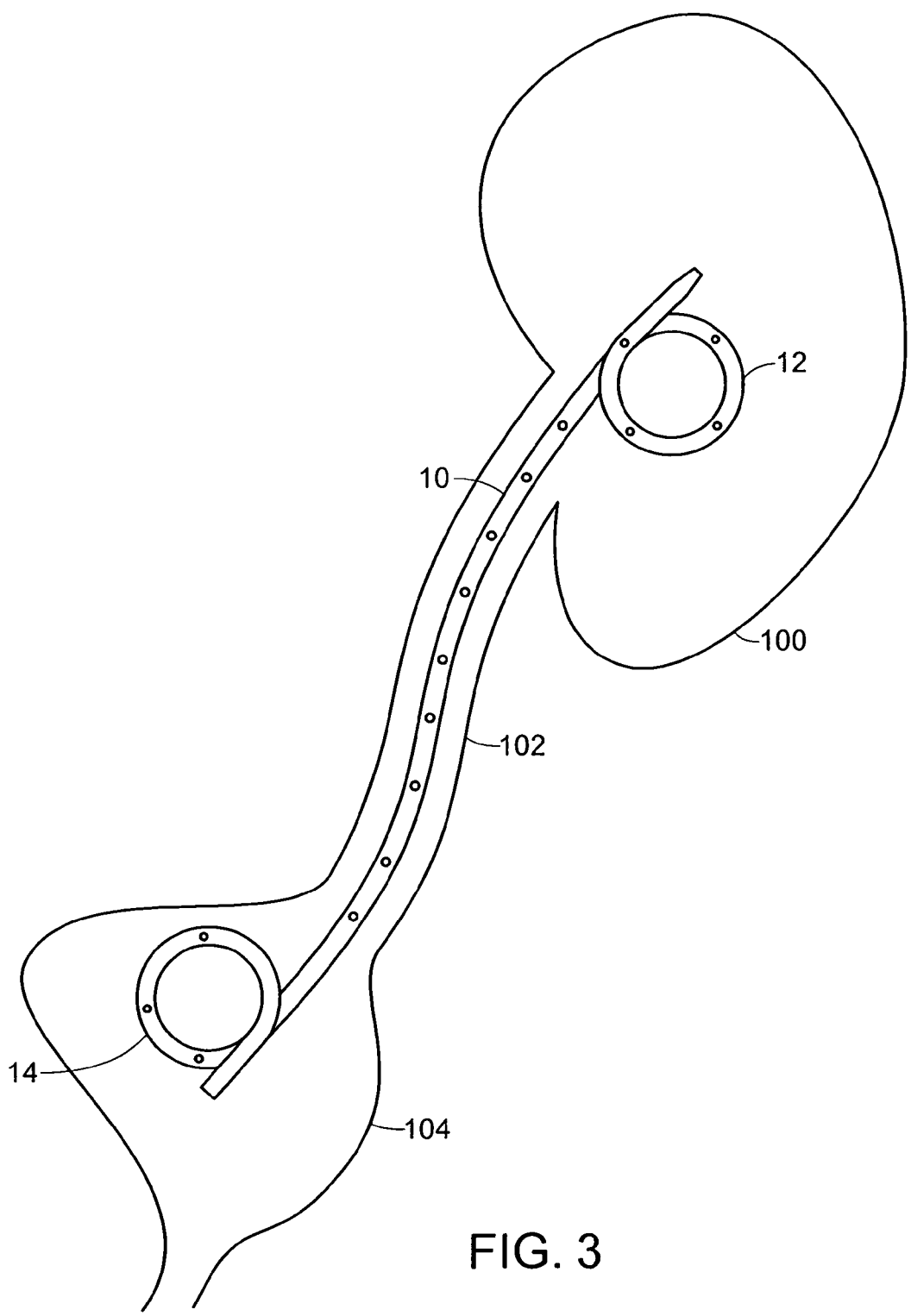
FIG. 3 is a schematic rendering of the stent of FIG. 1 in a kidney, ureter, and bladder.
Figure 4:
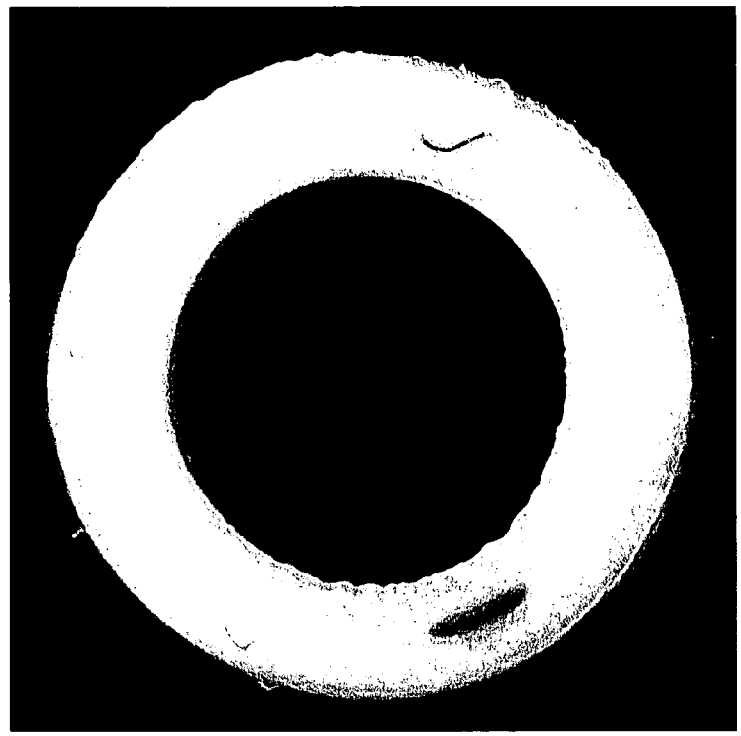
FIG. 4 is an image of a cross section of the embodiment of FIG. 1 taken along section line 4-4.
Figure 5:
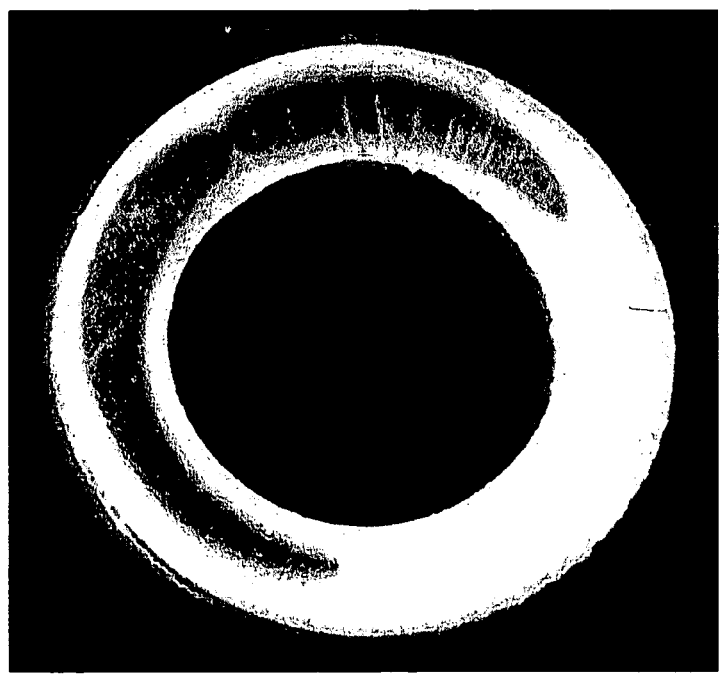
FIG. 5 is an image of a cross section of the embodiment of FIG. 1 taken along section line 5-5.
Figure 6:
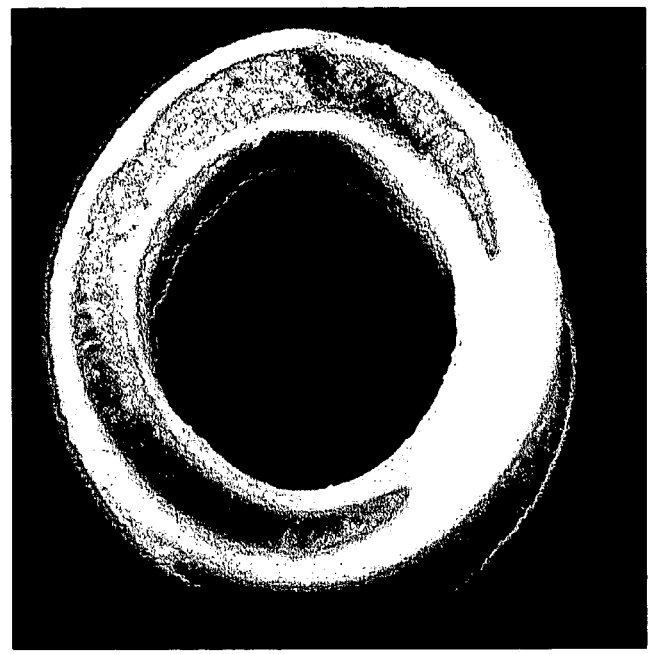
FIG. 6 is an image of a cross section of the embodiment of FIG. 1 taken along section line 6-6.
Figure 7:
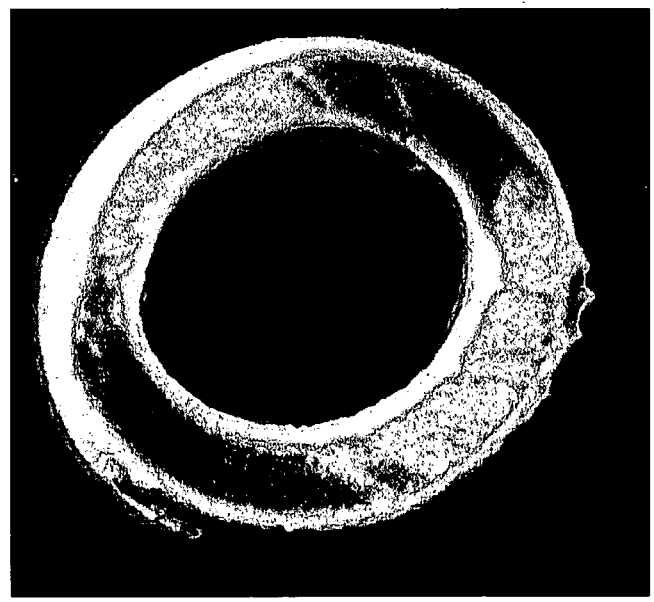
FIG. 7 is an image of a cross section of the embodiment of FIG. 1 taken along section line 7-7.
Figure 8:
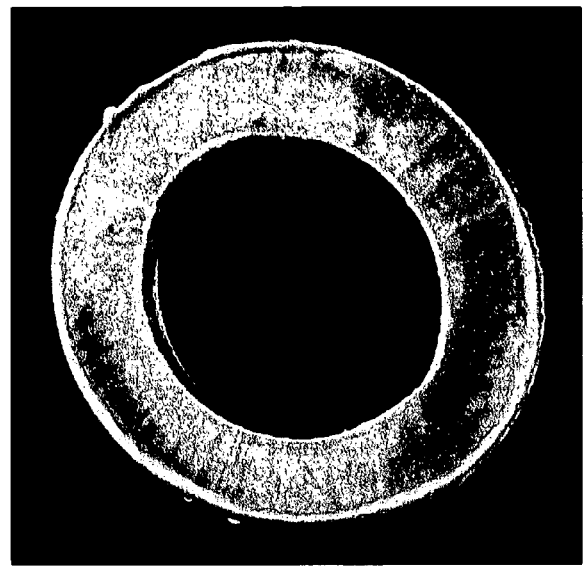
FIG. 8 is an image of a cross section of the embodiment of FIG. 1 taken along section line 8-8.

The third section 22 is formed from a coextrusion of the material(s) from which the first section 24 is made and the material(s) from which the second section 20 is made. As shown in FIG. 1, the third section 22 is closer to the first coil 14 than to the second coil 12. However, in alternative embodiments, the third section (i.e., a transition section where the material(s) making up one section of the stent transition to the material(s) making up another section of the stent) can be located anywhere along the length of the stent. The transition section typically is located between the coils on either end of the stent and is about 2 cm long to about 10 cm long. However, the transition section can be any length. The first section 24 includes a first material having a first durometer. The second section 20 includes a second material having a second durometer, which is greater than the first durometer value. Accordingly, the first section is "softer" than the second section. The third section 24 includes both the first and second materials, and the first and second materials are separate, distinct, and associated in an unsymmetrical, irregular configuration. In operation, the first coil 14 typically resides in the patient's bladder, and the second coil 12 typically resides in the patient's kidney (FIG. 3).

The stent 10 is a single piece and is sized to fit within a ureter. For example, two types of ethylene vinyl acetate ("EVA") can be extruded to form the stent. In a continuous process, the first section 24 is formed from one type of EVA; a transition section (i.e., the third section 22), then, is formed by gradually ceasing the deposition of the first type of EVA and gradually increasing the deposition of a second type of EVA; and the other end of the stent, the second section 20, is formed from the second type of EVA after the first type of EVA has ceased being extruded. Each type of EVA has a different durometer value, with the first type of EVA having a durometer value that is less than the durometer value of the second type of EVA. The two materials in the third section 22 are separate, are distinct, and are associated with each other in an irregular configuration. Additionally, other materials may be mixed with the first and/or second types of the EVA prior to extrusion. For example, radiopaque materials, such as bismuth subcarbonate, and/or colorants can be added. The addition can occur at the site of manufacture or a supplier can supply the EVA already compounded with the radiopaque material alone or with the colorant alone or with both the radiopaque material and the colorant. Even if these materials are mixed, the fact that one EVA type has a durometer value less than the second EVA type can mean that the section of the stent formed from the first type of EVA is "softer" than the section of the stent formed from the second type of EVA.

After extrusion, the curled portions are formed. For example, the extrusion can be placed on a mandrel, shaped in a particular form, and the extrusion can be formed into a desired shape by heating the extrusion while on the mandrel. Alternatively, the extrusion can be laid into a plate having a groove cut into it in the shape of the desired final product. The plate is heated from below (for example, with a heat lamp) to form the extrusion into a shape according to the configuration of the groove. Both coils can be formed at the same time using two adjacent plates, each with a groove for the coil at either end of the stent. The plates are heated at different temperatures, to the extent necessary, for example, if the two ends of the stent are made from different material (s), and can be heated for the same length of time. Additionally, after extrusion, holes can be bored into the stent by placing a nylon core inside the stent to prevent the stent from collapsing and drilling through the stent, for example, with a hollow sharpened bit.

FIGS. 4-8 show a series of cross-sectional views taken along the length of one of the stent 10. The approximate position of these cross-sections are shown in FIG. 1. It should be understood that the position of these cross-sections is merely an example. In various embodiments, the transition section of the medical stent can be relatively short, or relatively long, depending upon the physical characteristics of the stent that are desired. Additionally, sections taken in various embodiments may look different than the representations shown in FIGS. 4-8, depending upon, for example, the length of the transition section, the materials being extruded, and the method of co-extrusion used to manufacture the stent. Thus, the cross-sections shown in FIG. 1 and FIGS. 4-8 should be understood to illustrate both one embodiment of the invention and the general principle whereby the material(s) forming one section of the stent transition to the material(s) forming the other section of the stent. These figures show one material mixed with a colorant (for example, EVA and a colorant) (the darker portions of the cross-section) gradually increasing in abundance along the length of at least part of the stent and a second material not mixed with a colorant (for example, a second type of EVA) (the lighter portions of the cross-section) gradually decreasing in abundance along the length of at least part of the stent. Some of these views are indicative of the first and second materials being separate, distinct, and associating in an unsymmetrical, irregular configuration. In certain embodiments, the change in material composition can occur over any part of the shaft of the stent or all of the shaft of the stent. At least one of the materials can be ethylene vinyl acetate. Additionally, stents according to the invention can have several transition zones where materials change and/or can have more than two materials (or more than two mixtures of materials) that change along the length of the stent. For example, the shaft of a stent, or a portion thereof, may or may not be the same material(s) and/or the same durometer as either of the two coils. Moreover, each of the shaft and two coils can be formed from different material(s).

In certain embodiments, the material(s) that make up the second section of the stent (the harder section of the stent) can extend at least half way down the shaft of the stent, and can extend even further, such that the transition section (e.g., the third section in FIG. 1) is closer to the first coil (the coil in the softer section of the stent) than to the second coil (the coil in the harder section of the stent). Such a configuration enhances the placement characteristics of a stent because the preponderance of hard material(s) makes the stent stiffer and easier for a medical profession to place. In many embodiments, the transition of material(s) does not occur in one of the coils such that each coil is formed from a single material (or a single mixture of materials). However, the transition can occur anywhere along the length of the stent. Also in some embodiments, the inner diameter of the stent is maximized but not so much as to adversely impact the stent's ability to be pushed over a guidewire.

Interrupted layer extrusion techniques, gradient-type coextrusion techniques, or similar techniques can be used to produce the transition sections described above. Such extrusion techniques can be used instead of using joints or welds to bring together two ends of a stent, each end having a different physical property than the other end. Such joints or welds can fail during use of the stent and can be difficult to manufacture. Continuous material extrusion according to the invention enhances stent integrity while allowing for desired placement and drainage characteristics. Additionally, continuous extrusion products tend not to kink in the transition zone as might a stent with a butt-joint or a weld. In general, any type of thermoplastic polymer can be extruded such as a silicone, a polyurethane, or a polyolefin copolymer such as EVA. In general, in one embodiment of the invention, two types of EVA (at least one type of EVA can be mixed with a radiopaque material and at least one type of EVA can be mixed with a colorant) are extruded to form the stent. In a continuous process, one end of the stent is formed from one type of EVA (for example, the first section 24 in FIG. 1); a transition section (for example, the third section 22 in FIG. 1), then, is formed by gradually ceasing the deposition of the first type of EVA and gradually increasing the deposition of a second type of EVA; and the other end of the stent is formed from the second type of EVA (for example, the second section 20 in FIG. 1) after the first type of EVA has ceased being extruded. Each type of EVA has a different durometer value. The mixing of the two types of EVA in the transition section produces a section in which the two materials are separate, are distinct, and are associated with each other in an irregular configuration. After extrusion, the curled portions are formed.

Figure 12:
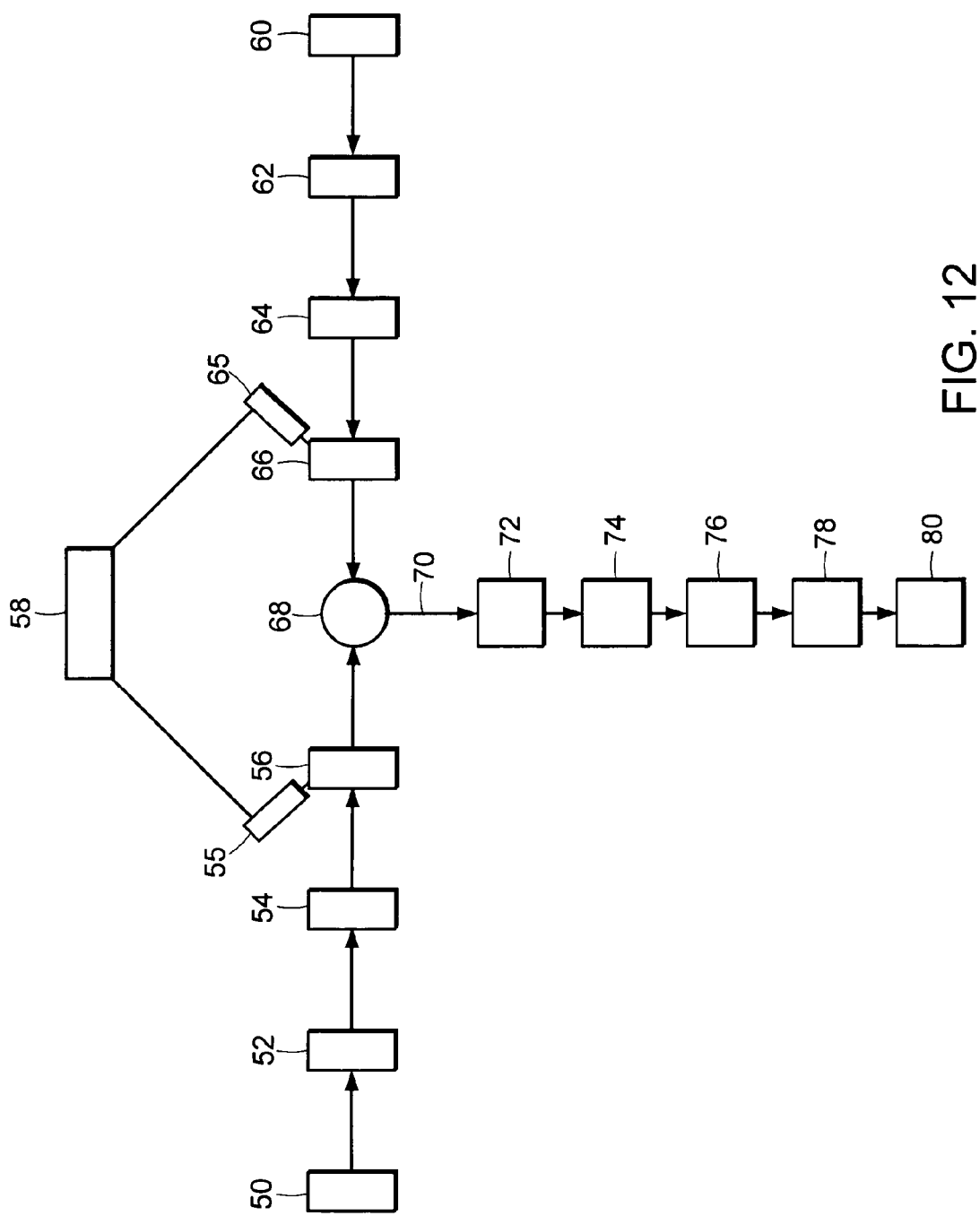
FIG. 12 is a schematic rendering of one system used to manufacture stents according to the invention.

In more detail and in one example of an extrusion technique as shown in FIG. 12, a gradient-type technique, a first pelletized type of EVA is placed in a first dryer 50 and a second pelletized type of EVA is placed in a second dryer 60. The dryers 50, 60 are hoppers to contain the pellets, and, to the extent necessary, to dry the pellets, and each dryer 50, 60 feeds the pellets to an extruder 52, 62. The two extruders 52, 62 melt the pellets, and each of the melted materials passes through a separate adapter 54, 64 to a separate melt pump 56, 66 (which are also referred to as a gear pumps). Each melt pump 56, 66 has a rotary gear which allows the melted materials to pass through the pump 56, 66. A computer 58 runs two servo motors 55, 65 that control the melt pumps 56, 66. The computer 58 controls the revolutions per minute as a function of the distance over which a point in the extruded product travels. There is a feedback loop between each melt pump 56, 66 and its related extruder 52, 62 such that when the pressure between the extruder 52, 62 and the melt pump 56, 66 is too high, the extruder 52, 62 shuts off. Each extruder 52, 62 is a slave to its respective melt pump 56, 66. The two separate lines, each containing a different EVA, come together at a cross-head 68. The cross-head 68 contains lumens that are separate from each other except for a relatively short distance in the cross-head 68. This distance is immediately adjacent a die and a tip where the extruded product exits the cross-head 68. The two materials only come together immediately adjacent to the die and the tip. The die dictates the outer diameter of the extruded product and the tip dictates the inner diameter of the product. The end of the tip is flush with the end of the die. Air is metered into a port that connects with the tip. Air from the tip pushes out the outer and inner diameters of the extruded product. Also, the tip is ported to the atmosphere to avoid the extruded product being flat. The extruded product (emerging from the cross-head 68 according to arrow 70) is then cooled in a quench tank 72, which is a water bath, to fix the product's shape. Next, the cooled product is dried with an air blower 74 and is measured with a laser micrometer 76. The laser micrometer 76 measures the outer diameter of the extruded product, and other gauges can be used to measure the inner diameter of the extruded product. The laser micrometer 76 is either monitored by an operator or is connected in a feedback control loop to control the final diameter of the extruded product. After passing through the laser micrometer 76, the extruded product is pulled through a "puller/cutter" machine 78. This device 78 pulls at a particular rate to control the shape of the extruded product, such as tapers on the ends of the extruded product, and cuts the extruded product to the correct length for a stent. Finally, a conveyer 80 separates the acceptable and unacceptable final products. Generally, if the diameter of the extruded product is too large according to the laser micrometer, the operator or the feedback loop will act to speed up the puller/cutter, decrease the extruder(s)/melt pump(s) output (s), and/or decrease the internal air support provided through the tip. If the diameter of the extruded product is too small, the operator or the feedback loop will act to slow down the puller/cutter, increase the extruder(s)/melt pump(s) output (s), and/or increase the internal air support provided through the tip. When the adjustments are made, the measurement of the inside diameter of the extruded product can be taken into account.

This system has at least three features. First, the entire system has no valves, and, specifically, the cross-head 68 has no moving parts such as valves. Second, extrusion can occur in a non-linear fashion, because the computer 58 and servo motors 55, 65 control the melt pumps 56, 66 on the basis of distance traveled. Thus, the melt pumps 56, 66 are "ramped up" or "ramped down" as necessary. Accordingly, a theoretically infinite gradient of material can be extruded by varying the pumping rates of the melt pumps 56, 66. And third, the process for combining the two EVA materials does not involve production of waste melted material as a byproduct of manufacture.

Through this machinery, in a continuous process, one end of the stent is formed from one type of EVA; a transition section, then, is formed by gradually ceasing the deposition of the first type of EVA and gradually increasing the deposition of a second type of EVA; and the other end of the stent is formed from the second type of EVA after the first type of EVA has ceased being extruded. Each type of EVA has a different durometer value. A radiopaque material and/or a colorant can be added to either of the EVA materials (the addition can occur at the site of manufacture or a supplier can supply the EVA already compounded with the radiopaque material, such as bismuth subcarbonate, alone or with the colorant alone or with both the radiopaque material and the colorant). The mixing of the two types of EVA in the transition section results in a section in which the two materials are separate, are distinct, and are associated with each other in an irregular configuration. After extrusion, the curled portions are formed. For example, the extrusion can be placed on a mandrel, shaped in a particular form, and the extrusion can be formed into a desired shape by heating the extrusion while on the mandrel. Alternatively, the extrusion can be laid into a plate having a groove cut into it in the shape of the desired final product. The plate is heated from below (for example, with a heat lamp) to form the extrusion into a shape according to the configuration of the groove. Both coils can be formed at the same time using two adjacent plates, each with a groove for the coil at either end of the stent. The plates are heated at different temperatures, to the extent necessary, for example, if the two ends of the stent are made from different material(s), and can be heated for the same length of time. Additionally, after extrusion, holes can be bored into the stent by placing a nylon core inside the stent to prevent the stent from collapsing and drilling through the stent, for example, with a hollow sharpened bit. The stent also can be covered in part or in its entirety with a lubricant. Useful coatings include those that are hydrophilic.

Various embodiments of medical stents according to the invention can have any of a variety of features. A dual durometer stent that incorporates a higher durometer value material (for example, firm EVA) for the renal coil and that gradually transitions into a lower durometer value material (for example, soft EVA) for the bladder coil is useful. For example, the "hard" material can be EVA having a durometer value of about 80 to about 95 on a Shore A scale, preferably about 87 to about 95 on a Shore A scale, and more preferably about 90 on a Shore A scale, and the "soft" material can be another type of EVA having a durometer value of about 70 to about 90 on a Shore A scale, preferably about 78 to about 90 on a Shore A scale, and more preferably about 86 on a Shore A scale. These values are examples of a more general principle, namely, having a stent with a harder end and a softer end. Other materials or EVA having a durometer value different than that described above can be useful. In some embodiments, the materials forming the stent, such as the two types of EVA, are mixed with other materials. For example, as described above, each type of EVA can be mixed with a radiopaque material, such as bismuth subcarbonate, or a colorant. The radiopaque material allows a medical professional to place the stent under the guidance of an x-ray device and fluoroscope or other similar device where the radiopaque material appears on a view screen because it blocks or reflects x-ray energy. The colorant also can be used as a visual cue to a medical professional about the location of the stent in the patient.

Another way to describe the two ends of the stent are by the coil retention strength of each coil of the stent. For example, such retention strengths can be used as a measure of the ability to resist migration within a patient, or, more broadly, as a measure of how "hard" or how "soft" the ends of the stent are. One way to determine retention strength is found in American Society for Testing and Materials (ASTM) Designation F 1828-97: Standard Specification for Ureteral Stents, approved Nov. 10, 1997, and published May, 1998, the disclosure of which is incorporated herein by reference. This specification covers single-use ureteral stents with retaining means at both ends, during short term use for drainage of urine from the kidney to the bladder. These stents typically have diameters of 3.7 French to 14.0 French, lengths of 8 cm to 30 cm, and are made of silicone, polyurethane, and other polymers. They are provided non-sterile for sterilization and sterile for single-use. It is noted that this ASTM standard excludes long-term, indwelling usage (over thirty days), use of ureteral stents for non-ureteral applications, and non-sterile stents. Nevertheless, even if stents according to the invention meet any of these exclusions, or do not otherwise fall under the scope of this ASTM standard, to the extent those skilled in the art understand it to be reasonable to use the coil retention strength test method described in this document, the test method can be used.

The retention strength test method (section 6.2 of the ASTM document) involves using a funnel block submerged in a water bath at approximately 37 degrees Celsius. The funnel block is a block of TEFLON or DERLIN defining a funnel. The funnel is two inches at its widest diameter and, in cross section, has walls that form an approximately 60 degree angle. The funnel narrows to a bore slightly larger than the specimen to be tested, and this bore is about 0.675 inches long. There must be clearance between the outside diameter of the test specimen and the inside diameter of the hole in the funnel block through which the specimen is pulled. For example, for stents of 3.7 to 8.5 French, a funnel bore should be 0.125 inches (3.16 mm) in diameter; for stents of 10.0 French, a funnel bore should be 0.159 inches (4.04 mm) in diameter; and for stent of 14.0 French, a funnel bore should be 0.210 inches (5.33 mm) in diameter. The test specimen is removed from its sterile packaging, and the retention means (for example, a coil at the end of the stent) of the specimen is straightened with an appropriate guidewire. The test specimen is soaked for at least thirty days and is cut to allow a straight portion of the stent to be inserted upwards through the funnel fixture into the grip of a tensile test machine without loading the retention mechanism of the stent to be tested. Prior to inserting the test specimen, the test specimen is submerged in the water bath for at least one minute to allow it to reach thermal equilibrium. If the material is significantly effected by moisture, the test specimen should be allowed to equilibrate for a minimum of 24 hours. The straight portion of the stent then is inserted through the bottom of the funnel and into the grip. If testing 30 days after opening the package, the retention means is not straightened prior to testing. Then, the specimen is pulled up through the funnel at 20 inches/minute. The maximum force required to pull the stent completely through the funnel is recorded.

Referring to FIG. 10, a table is provided that compares one stent embodiment according to the invention to other stents. The retention strength of the renal coil (for example, but without limitation, the second coil 12 in FIG. 1) for the various stents in various sizes is determined using the test method described above. The bladder coil (for example, but without limitation, the first coil 14 in FIG. 1) retention strength of the embodiment of the invention described in FIG. 10 would be less than or equal to the renal coil strength provided in FIG. 10. In one embodiment, the retention strength of the bladder coil approximates those values provided in FIG. 10 for the Contour™ stent. These values are examples and are not limiting. Other retention strengths are possible, depending upon the method of manufacture or other considerations. However, typically, retention strengths of the two coils are chosen such that the retention strength of the coil placed in the kidney is greater than the retention strength of the coil placed in the bladder. A retention strength of at least about 10 gram-force or more is desirable in many embodiments.

Some embodiments of stents according to the invention can have an outer diameter from about four to about nine French with lengths of from about ten to about thirty centimeters as measured between the coils. FIG. 11 shows an example of some suitable French sizes along with the size of the inner and outer diameters. Unless otherwise noted, the dimensions in FIG. 11 are in inches. The notation "O.D." refers to outer diameter and the notation "I.D." refers to inner diameter. In certain embodiments, stents with standard outer diameter sizes can have inner diameters (i.e., the diameter of a lumen) that are larger than standard inner diameters normally present in those standard outer diameters. This configuration facilitates passage of the stent over the guidewire and increases the drainage allowed by the stent. For example, a four French stent can have an inner diameter equivalent to that found in a 4.8 French stent to increase drainage and to facilitate a 0.35 inch and/or a 0.38 inch guidewire, and/or a five French stent can have an inner diameter equivalent to a six French stent to facilitate a 0.35 inch and/or a 0.38 inch guidewire and increase drainage.

Figure 9:
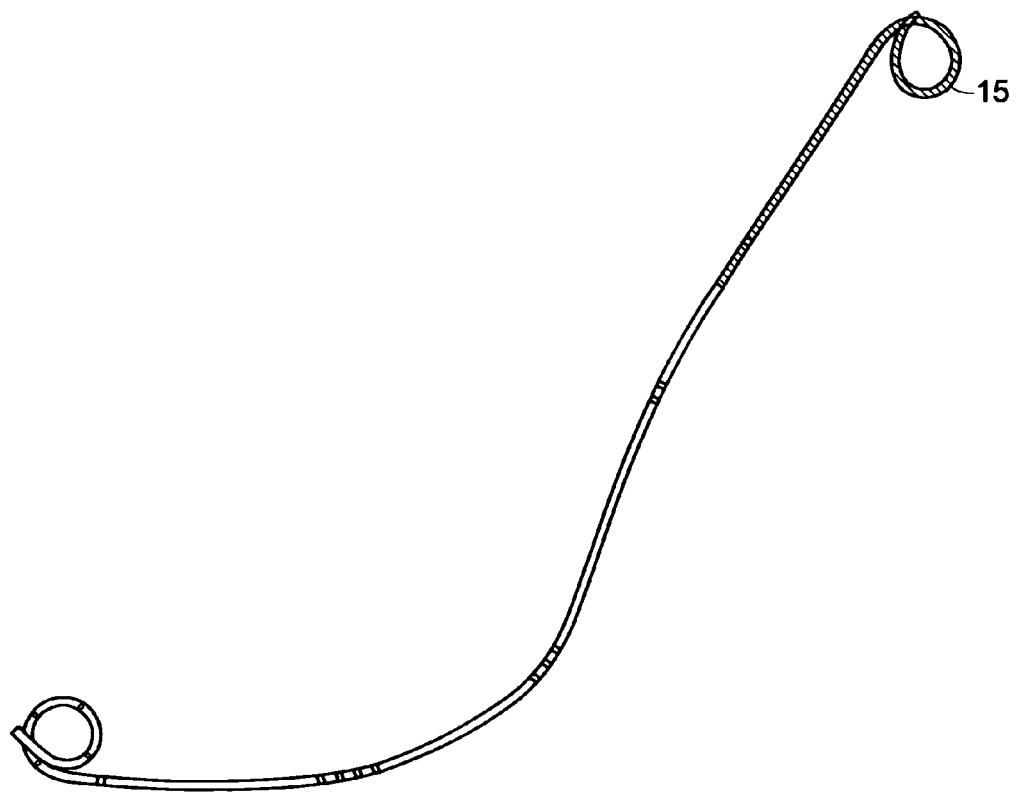
FIG. 9 is a schematic rendering of one embodiment of a stent according to the invention.

The stent can have graduation marks and stent size imprinted on stent. For example, one marking pattern is shown in FIG. 9. This stent also has a slightly asymmetrical coil 15 which makes more than one revolution. This coil is the coil to be placed in the kidney (although in other embodiments, the asymmetrical coil can be the one to be placed in the bladder, or both coils). The taper of the renal coil is relatively long. Sizing information and marks about every 5 cm are used as an inking pattern. Two marks are used for 5 cm; three marks are used for 10 cm; four marks are used for 15 cm; and one thick mark is used to indicate the beginning of the bladder coil. Also, a radiopaque band can be included on some stents. Also, in certain embodiments of the invention, the renal coil retention strength can measure about 25-30 gram-force. The shaft and bladder coil can be softer, having a coil retention strength of about 14 gram-force. However, the shaft, or a portion thereof, may or may not be made from material(s) of the same durometer as either of the two coils (for example, to stiffen the shaft to facilitate placement of the stent).

In operation, the distal end of the stent 10 is inserted through the bladder 104 and ureter 102 into the kidney 100. For example, a medical professional inserts a guidewire (not shown) through the bladder 104, ureter 102 and kidney 100 of a patient. The stent 10 is placed over the guidewire, thereby uncurling the coils 12, 14 to the straightened position. The stent 10 slides along the guidewire, and the guidewire is sufficiently stiff to hold the coils 12, 14 in a straight configuration (e.g., the proximal coil in a straightened position 26, FIG. 1) while the guidewire is in the lumen of the stent 10. A pusher (optionally with a radiopaque band) that slides over the guidewire, behind the stent 10, abuts the end of the stent and is used to push the stent 10 over the guidewire. The radiopaque band, if used, allows a medical professional to view the pusher on a fluoroscope, particularly where it abuts the stent, using x-rays. Additionally, if the stent 10 is radiopaque, placement of the stent in the patient can be confirmed by viewing the stent on a fluoroscope. Once at least a portion of the second section 20 is positioned within the kidney 100, the guidewire is withdrawn. If a pusher is used, the pusher holds the stent in place while the guidewire is removed. The shape-memory material from which second coil 12 is constructed allows the second section 20 in a straightened position to return to its coiled shape in the kidney 100 once the guidewire is withdrawn. A similar re-coiling of the first coil 14 also occurs in the bladder 104 when the guidewire is withdrawn from that area of the stent 10. Thus, the "hard" coil 12 is placed in the kidney 100, and the "soft" coil 14 is placed in the bladder 104. Stents can be provided as a kit with a guidewire and/or a pusher.

The tapered tip on the second coil 14 (the renal coil) can facilitate inserting the stent through the passages of the patient's body. Additionally, a medical professional can use the suture 18 to reposition the stent (by pulling on it) when inserting the stent, and the medical professional can use the suture 18 to remove the stent from the patient. For example, the medical professional either leaves the suture inside the patient's body or leaves the end of the suture outside the body. When the stent 10 is to be removed, the medical professional pulls on the suture 18, removing the stent. However, the suture 18 does not have to be used to remove the stent 10.

When placed in a patient's body, stents according to the invention may soften slightly, as might many thermoplastic materials when exposed to elevated temperatures, for example, but without limitation, by about 30% or less, or about 20% or less, or about 10% or less, or about 5% or less. However, such softening is not substantial. Softening can be measured by methods known in the art. For example, the ASTM test method described herein may be adapted to determine if coils soften by determining if body temperature conditions cause a decrease in retention strength relative to room temperature conditions. However, other methods may be used.

An alternative method to straighten the coil 12 of the second section 20 is to produce relative movement between a straightening device (e.g., a sheath) and second section 20, such that the straightening device moves distally relative to the second section 20, thereby uncurling the coil 12 to a straightened position. Once at least some portion of the second section 20 is positioned within the kidney 100, the straightening device is removed. The second section 20 is constructed from a shape-memory material. Thus, once the straightening device is withdrawn, the coil 12 in the straightened position returns to its coiled shape. A similar re-coiling of the first coil 14 also occurs when the straightening device is withdrawn from that area of the stent 10. Other modes of inserting and/or straightening a device also are useful.

Variations, modifications, and other implementations of what is described herein will occur to those of ordinary skill in the art without departing from the spirit and the scope of the invention. Accordingly, the invention is to be defined not only by the preceding illustrative description.

What is claimed is:

1. A medical stent comprising:
   a single-piece stent body comprising:
   a first section defining a lumen and comprising a first retention structure, the first section comprising a first material having a first durometer value;
   a second section defining a lumen and comprising a second retention structure, the second section comprising a second material having a second durometer value, wherein the second durometer value is greater than the first durometer value; and
   a third section defining a lumen having a longitudinal axis, the third section located between the first and second sections, wherein the third section comprises a co-extrusion of the first and second materials, the first material and the second material being distinct from each other and arranged substantially asymmetrically within a plane normal to the longitudinal axis, the relative amount of the first material and the second material within the third section varying non-linearly within a plane parallel to the longitudinal axis.

2. The stent of claim 1 wherein the first material comprises ethylene vinyl acetate.

3. The stent of claim 1 wherein the first material has a durometer value of about 70 to about 90 on a Shore A scale.

4. The stent of claim 1 wherein the second material has a durometer value of about 80 to about 95 on a Shore A scale.

5. The stent of claim 1 wherein a cross-section of the lumen in at least one of the first, second, and third sections is circular.

6. The stent of claim 1 wherein a cross-section of at least one of the first, second, and third sections is circular.

7. The stent of claim 1 wherein at least one of the first, second, and third section comprises a radiopaque material.

8. The stent of claim 1 wherein the stent body does not substantially soften when exposed to a temperature of a human body.

9. The stent of claim 1 wherein at least a portion of the stent body is sized for placement in a ureter.

10. The stent of claim 1 wherein an outer surface of the third section smoothly transitions to outer surfaces of the first and second sections immediately proximate the third section and an inner diameter of the third section is substantially constant through the third section and on either side of the third section immediately proximate to the third section in the first and second sections.

11. The stent of claim 1 wherein an inner diameter of third section is substantially constant through the third section and on either side of the third section immediately proximate to the third section in the first and second sections.

12. The stent of claim 1, wherein the first section is devoid of the second material.

13. The stent of claim 1, wherein the second section is devoid of the first material.

14. A medical stent comprising:
   a single-piece stent body comprising:
   a first section defining a lumen and comprising a first retention structure, the first section comprising a first material having a first retention strength;
   a second section defining a lumen and comprising a second retention structure, the second section comprising a second material having a second retention strength, wherein the second retention strength is greater than the first retention strength; and
   a third section defining a lumen having a longitudinal axis, the third section located between the first and second sections, wherein the third section comprises a co-extrusion of the first and second materials, the first material and the second material being distinct from each other and arranged substantially asymmetrically within a plane normal to the longitudinal axis, the amount of any one of the first material or the second material within the third section varying non-linearly within a plane parallel to the longitudinal axis.

15. The stent of claim 14 wherein the stent body does not substantially soften when exposed to a temperature of a human body.

16. The stent of claim 14 wherein at least a portion of the stent body is sized for placement in a ureter.

17. The stent of claim 14 wherein an outer surface of the third section smoothly transitions to outer surfaces of the first and second sections immediately proximate the third section.

18. The stent of claim 14 wherein an inner diameter of the third section is substantially constant through the third section and on either side of the third section immediately proximate to the third section in the first and second sections.

19. The stent of claim 14, wherein the first section is devoid of the second material and the second section is devoid of the first material.

20. A method for placing a medical stent comprising:
inserting a medical stent into a ureter, the medical stent comprising:
a single-piece stent body comprising:
a first section defining a lumen and comprising a first retention structure, the first section comprising a first material having a first durometer value;
a second section defining a lumen and comprising a second retention structure, the second section comprising a second material having a second durometer value, wherein the second durometer value is greater than the first durometer value; and
a third section defining a lumen having a longitudinal axis, the third section located between the first and second sections, wherein the third section comprises a co-extrusion of the first and second materials the first material and the second material being distinct from each other and arranged substantially asymmetrically within a plane normal to the longitudinal axis, the amount of any one of the first material or the second material within the third section varying non-linearly within a plane parallel to the longitudinal axis.

* * * * *